United States Patent [19]
Seidelmann et al.

[11] Patent Number: 6,127,368
[45] Date of Patent: Oct. 3, 2000

[54] ANELLATED β-CARBOLINES

[75] Inventors: Dieter Seidelmann; Andreas Huth, both of Berlin, Germany; Preben Olesen, Kobenhaven, Denmark; Eckhard Ottow, Berlin, Germany; Jonathan Turner, Berlin, Germany; Margrit Hillmann, Berlin, Germany; Belinda Cole, Berlin, Germany

[73] Assignee: Schering Aktiengesellschaft, Germany

[21] Appl. No.: 08/930,908

[22] PCT Filed: Apr. 3, 1996

[86] PCT No.: PCT/DE96/00632

§ 371 Date: Aug. 6, 1998

§ 102(e) Date: Aug. 6, 1998

[87] PCT Pub. No.: WO96/32392

PCT Pub. Date: Oct. 17, 1996

[30] Foreign Application Priority Data

Apr. 12, 1995 [DE] Germany ............................ 195 14 524

[51] Int. Cl.[7] ........................ A61K 31/495; A61K 31/44; C07D 241/36; C07D 471/00
[52] U.S. Cl. .......................... 514/249; 544/343; 544/345; 544/342; 514/253.02; 514/252.1; 514/249; 514/287; 514/70; 546/64
[58] Field of Search ................... 546/64, 65, 70; 544/343, 345, 342; 514/253.02, 252.1, 249, 287

[56] References Cited

FOREIGN PATENT DOCUMENTS

4130933A1    9/1991    Germany .

OTHER PUBLICATIONS

Agarwal, et. al., Indian J. Chem., Sect. B, Antiparasitic agents. Part X. Synthesis of 2,7-disubstituted-1,6-dihydropyrido[3,4-b]imidazo[4,5-e]indoles as anthelmintic agents, pp. 843–847, 1990.

*Primary Examiner*—John Kight
*Assistant Examiner*—Binta Robinson
*Attorney, Agent, or Firm*—Millen, White, Zelano & Branigan, P.C.

[57] ABSTRACT

Compounds of formula I

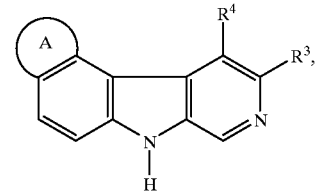

(I)

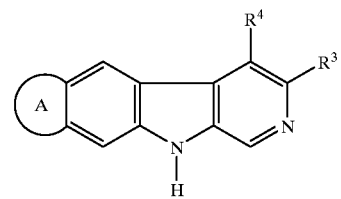

are described, as well as the process for their production and their use in pharmaceutical agents.

19 Claims, No Drawings

ANELLATED β-CARBOLINES

This application is a 371 of PCT/DE96/00632 filed Apr. 3, 1996.

The invention relates to anellated β-carbolines, their production and use in pharmaceutical agents.

It is known from numerous publications that β-carbolines have an affinity to the benzodiazepine receptors, although they differ structurally from benzodiazepines, and that they are used as psychopharmaceutical agents because of the affinity to the BDZ receptors. β-Carbolines can have an antagonistic, agonistic or inversely agonistic effect on the properties that are known of BDZ receptors.

It has now been found that the compounds according to the invention have a very good affinity to the benzodiazepine receptors and have a specific inverse agonistic effect on the properties that are known regarding benzodiazepines. The compounds have anxiolytic, anti-amnestic and nootropic activities and improve learning and attentiveness. Because of their action profile, the compounds according to the invention are suitable for the production of pharmaceutical agents for treating geriatric symptoms, as well as to mitigate cognitive deficits and increase vigilance, without serious side effects occurring.

The invention relates to the compounds of formula I, their isomers, tautomers and salts

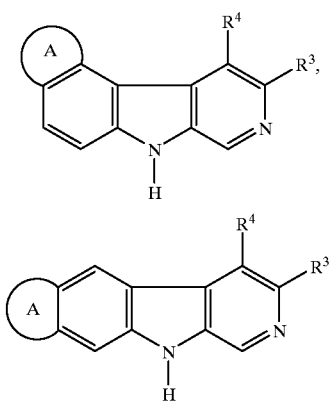

in which $R^3$ means hydrogen, $C_{1-6}$ alkyl, —CO—$R^1$, —C≡N, phenyl, which optionally is substituted one to three times with $C_{1-4}$ alkyl, $C_{1-4}$ alkoxy, halogen or —$CF_3$,

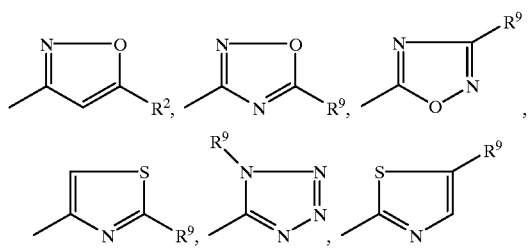

$R^4$ means hydrogen, $C_{1-6}$ alkyl, $C_{1-4}$ alkoxy-$C_{1-2}$ alkyl,

A represents a 5- to 6-membered unsaturated ring, in which 1–2 C atoms can be replaced by N, O and/or S and can be substituted with $R^5$ and $R^6$, and $R^5$ and $R^6$ are the same or different and mean hydrogen, $C_{1-6}$ alkyl, $C_{1-6}$ alkoxy, hydroxy, which can be functionally modified, $NR^7R^8$, COR, $C_{1-6}$ alkyl, which is substituted with optionally functionally modified hydroxy, $C_{1-4}$ alkoxy or halogens, a $C_{6-12}$ aryl or a 5- to 6-membered hetaryl radical, which contains one to three N, O and/or S atoms, and the aryl and hetaryl radical can be substituted with $C_{1-4}$ alkyl, $C_{1-4}$ alkoxy, halogen or $CF_3$, or $R^5$ and $R^6$ together mean a —$(CH_2)_n$ group and $R^1$ and R mean hydroxy, $C_{1-6}$ alkoxy or $NR^{10}R^{11}$, $R^2$ means hydrogen, $C_{1-4}$ alkyl or $C_{1-4}$ alkoxy-$C_{1-2}$ alkyl, $R^9$ means hydrogen or $C_{1-6}$ alkyl, n means 3 or 4, $R^7$ and $R^8$ each mean hydrogen, $C_{1-6}$ alkyl, acyl or phenyl, which can be substituted with $C_{1-4}$ alkyl, $C_{1-4}$ alkoxy, halogen or $CF_3$, $R^{10}$ and $R^{11}$ each mean hydrogen, $C_{1-6}$ alkyl, $C_{3-7}$ cycloalkyl or a $C_{6-12}$ aryl radical or a 5- to 6-membered hetaryl radical, which contains one to three N, O and/or S atoms, and the aryl and hetaryl radical can be substituted with $C_{1-4}$ alkyl, $C_{1-4}$ alkoxy, halogen or $CF_3$.

Alkyl contains respectively both straight-chain and branched-chain radicals, such as, for example, methyl, ethyl, propyl, isopropyl, butyl, isobutyl, sec-butyl, tert-butyl, pentyl, isopentyl and hexyl.

As aryl radicals $R^5$, $R^6$, $R^{10}$ or $R^{11}$, there can be mentioned, for example, phenyl, biphenyl and α- or β-naphthyl, which optionally are substituted in 1 to 3 places.

If $R^5$, $R^6$, $R^{10}$ or $R^{11}$ means a hetaryl radical, six-membered ring heteroaromatic compounds with up to 3 nitrogen atoms and five-membered ring heteroaromatic compounds with one to two oxygen, sulfur and/or nitrogen atoms are meant, such as, for example, triazine, pyridine, pyrimidine, pyrazine, pyridazine, furan, thiophene, pyrrole, imidazole, thiazole, 1,2,4-oxadiazolyl, 1,3,4-oxadiazolyl, which can be substituted in each case in 1 to 3 places.

Halogen is defined respectively as fluorine, chlorine, bromine and iodine. Cycloalkyl respectively stands for cyclopropyl, cyclobutyl, cyclopentyl, cyclohexyl, cycloheptyl.

Alkyl radical $R^5$, $R^6$ can be substituted in 1 to 3 places or else be present in perhalogenated form.

The hydroxy groups can be functionally modified, for example, by etherification or esterification. As ether and acyl radicals, the radicals that are known to one skilled in the art are considered. Preferred are easily cleavable ether radicals, such as, for example, the tetrahydropyranyl, tetrahydrofuranyl, tert-butyldimethylsilyl, tert-butyldiphenylsilyl, tribenzylsilyl radical. As acyl radicals, for example, $C_{1-6}$ alkanoyls such as acetyl, propionyl, butyryl and benzoyl are suitable.

If several hydroxy groups are present, cyclic acetals or ketals can be present, such as 1,3-dioxane or 1,3-dioxolane radicals, such as 2-phenyl-1,3-dioxane, 2,2-dimethyl-1,3-dioxolane, which are produced, for example, by reaction with acetone, an enol ether, 1,1-alkyl dihalide or acetone dimethyl ketal.

Acyl group $R^7$ or $R^8$ contains aromatic and aliphatic acyl groups such as benzoyl and benzoyls that are substituted in one to three places, as well as straight-chain or branched alkanoyls with up to 6 carbon atoms.

If A contains a heteroaromatic five-membered ring, the latter can have the following groupings:

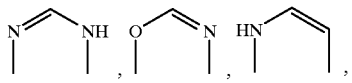

-continued

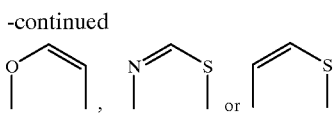

As heteroaromatic six-membered rings, there can be mentioned, for example, the following groupings:

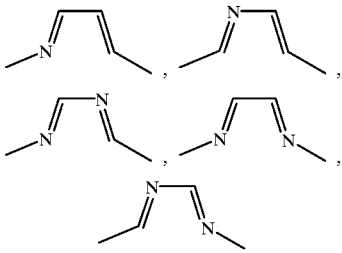

Substituents $R^5$ and $R^6$ can each be in any position on radical A or its tautomeric or isomeric forms. As preferred embodiments of $R^3$, —$COR^1$ is to be considered, and as preferred embodiments of $R^1$ and R, hydroxy and $C_{1-6}$ alkoxy are to be considered.

If a basic function is present, the physiologically compatible salts are derived from inorganic and organic acids. Suitable are inorganic acids, such as, for example, hydrochloric acid, hydrobromic acid, sulfuric acid or organic acids, such as, for example, aliphatic or aromatic mono- or dicarboxylic acids, such as formic acid, acetic acid, maleic acid, fumaric acid, succinic acid, lactic acid, tartaric acid, citric acid, oxalic acid, glyoxylic acid or sulfonic acids, for example, $C_{1-4}$ alkanesulfonic acids, such as methanesulfonic acid or benzenesulfonic acids, optionally substituted by halogen or $C_{1-4}$, such as p-toluenesulfonic acid.

If an acid function is present, the physiologically compatible salts of organic bases are suitable as salts, such as, for example, the readily soluble alkali and alkaline-earth salts, as well as N-methylglucamine, dimethylglucamine, ethylglucamine, lysine, 1,6-hexadiamine, ethanolamine, glucosamine, sarcosine, serinol, tris-hydroxymethylaminomethane, aminopropanediol, Sovak base, 1-amino-2,3,4-butanetriol.

The compounds of formula I as well as their salts can be used as pharmaceutical agents because of their affinity to benzodiazepine receptors. They have different intrinsic action (i.e., agonistic, antagonistic and/or inversely agonistic action) on various isoforms of the GABA-benzodiazepine receptor.

To use the compounds according to the invention as pharmaceutical agents, the latter are brought into the form of a pharmaceutical preparation, which, in addition to the active ingredient for enteral or parenteral administration, contains suitable pharmaceutical, organic or inorganic inert vehicles, such as, for example, water, gelatin, gum arabic, lactose, starch, magnesium stearate, talc, vegetable oils, polyalkylene glycols, etc. The pharmaceutical preparations can be present in solid form, for example, as tablets, coated tablets, suppositories, capsules, or in liquid form, for example, as solutions, suspensions or emulsions. Moreover, they optionally contain adjuvants, such as preservatives, stabilizers, wetting agents or emulsifiers, salts for changing the osmotic pressure or buffers.

For parenteral use, especially injection solutions or suspensions, especially aqueous solutions of active compounds in polyhydroxyethoxylated castor oil, are suitable.

As vehicle systems, surface-active adjuvants, such as salts of bile acids or animal or plant phospholipids, but also their mixtures as well as liposomes or their components can be used.

For oral use, especially tablets, coated tablets or capsules with talc and/or hydrocarbon vehicles or binders, such as, for example, lactose, corn or potato starch, are suitable. The use can also take place in liquid form, such as, for example, as juice, to which optionally a sweetener is added. The compounds according to the invention are introduced in a dosage unit of 0.05 to 100 mg of active substance in a physiologically compatible vehicle.

The dosage of the active ingredients can vary depending on the method of administration, age and weight of the patient, type and severity of the disease to be treated and similar factors. The daily dose is 0.1–300 mg, preferably 0.1–30 mg, whereby the dose can be given as a single dose to be administered one time or divided into 2 or more daily doses.

The production of the compounds according to the invention is carried out according to methods that are known in the art. For example, compounds of formula I are attained in that a) a compound of formula II

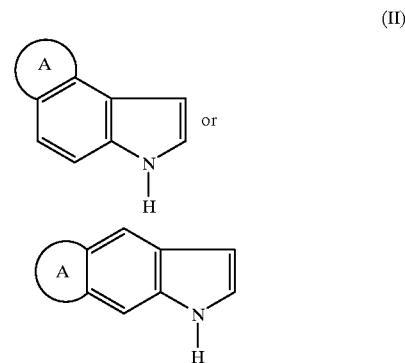

is reacted with a 2-azadiene of formula III

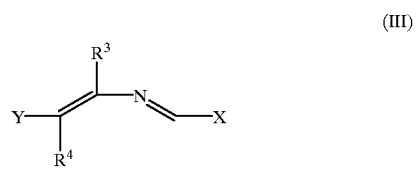

in which $R^3$, $R^4$ and A have the above meaning, and X and Y represent leaving groups, in the presence of acids or b) a compound of formula IV

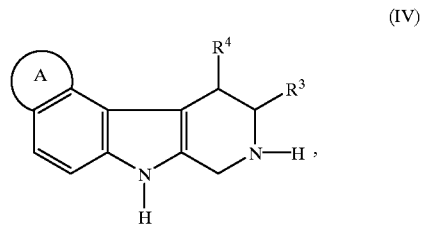

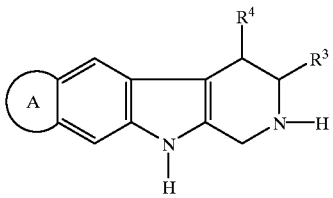

in which $R^3$, $R^4$ and A have the above meaning, is aromatized or c) a compound of formula V (V)

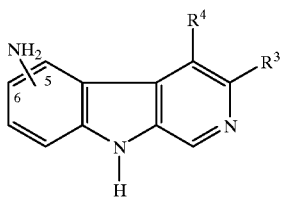

in which $R^3$ and $R^4$ have the above meaning, is reacted with an α,β-unsaturated aldehyde to a fused pyridine or reacted with a primary amine $H_2N-CH_2-R^5$ to a fused imidazole or the diazonium salts that are obtained with nitrites are reacted with acetoacetic acid derivatives to an ethylidenehydrazine derivative and the latter is cyclized to pyrrole or reacted with thiocyanate or isothiocyanate derivatives to a fused thiazole or d) a compound of formula VI (VI)

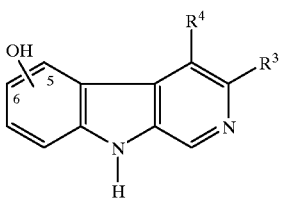

in which $R^3$ and $R^4$ have the above meaning, is reacted with a primary amine $H_2N-CH_2-R^5$ to a fused oxazole or with a vicinal primary diamine

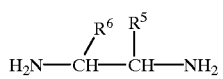

to a fused pyrazine or e) a nitrile oxide of formula VII (VII)

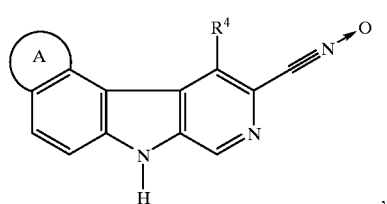

is cyclized with an acetylene derivative $\equiv-R^2$ to an isoxazole derivative, f) an α-haloketone of formula VIII (VIII)

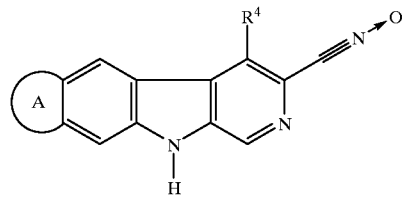

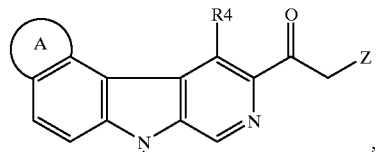

in which $R^4$ and A have the above meaning and Z is halogen, is reacted with a thioamide $H_2N-CS-R^9$ to a compound with $R^3$ meaning thiazolyl or g) a nitrile of formula IX (IX)

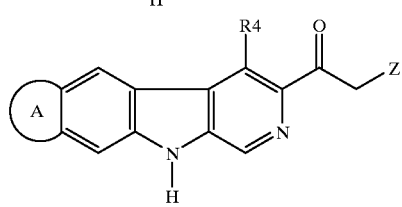

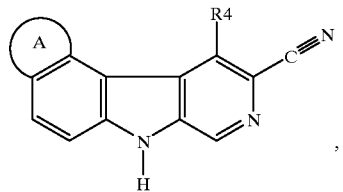

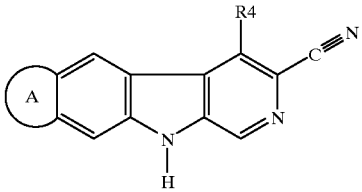

in which $R^4$ and A have the above meaning, is cyclized with an azide to a compound with $R^3$ meaning tetrazolyl and optionally then an ester group is saponified or reesterified, a carboxyl group is esterified, an amino group is alkylated or acylated, a functionally modified hydroxy group is released, the isomers are separated or the physiologically compatible salts are formed.

The reaction according to the invention of compounds of formula II with 2-azadienes of formula III to the compounds of formula I according to process a) is carried out according to EP-A-110813 in the presence of acids at temperatures of 0 to 150° C. Leaving groups X and Y can be the same or different; especially suitable are $C_{1-3}$ dialkylamines, such as dimethylamine, diethylamine and diisopropylamine, and cyclic amines, such as pyrrolidine.

The reaction is performed, for example, so that the indole derivative and the azadiene first is stirred at room temperature in an organic acid, such as, for example, formic acid, acetic acid, propionic acid or trifluoroacetic acid, and then is heated up to boiling temperature of the reaction mixture.

The acid can be used simultaneously as reactant and as solvent. Solvents such as, for example, alcohols, ethers, ketones, esters, such as ethyl acetate, hydrocarbons, such as toluene, or halogenated hydrocarbons, such as carbon tetrachloride, however, can also be added.

The amount of acid can be varied within wide limits, but it is used in excess. Preferably, a 3 to 10-fold acid excess, relative to the azadiene, is selected.

The molar ratios of indole and azadiene are not critical for the success of the reaction. In general, approximately equal molar amounts of the reactants are used, whereby quantitative ratios of 1 mol of aniline and 1–3 mol of azadiene are preferred. The reaction according to the invention can basically also be performed in the above-indicated solvents with catalytic amounts of mineral acids, such as sulfuric acid, hydrochloric acid, perchloric acid or organic acids, such as p-toluenesulfonic acid and trifluoroacetic acid.

To aromatize the compounds of formula IV, the processes that are known regarding the β-carbolines are suitable, such as, for example, the dehydrogenation with tert-butyl hypochlorite (EP-A- 190 987) or with trichloroisocyanuric acid (WO 94/12 498).

The fusing of unsaturated ring A according to process variants c) and d) is carried out as a function of the position of the amino or hydroxy group in 5,6- or 6,7-position of the β-carboline, preferably in 5,6-position. Optionally accumulating isomer mixtures are separated in the usual way by fractionated crystallization or chromatography.

If a pyridine ring is synthesized, this can be carried out according to the synthesis of Skraup [G. Alunni-Bistocchi et al. J. Chem. Soc. Perkin Trans. 1, 2935 (1992)], by, for example, an α,β-unsaturated aldehyde, which can be produced intermediately, being added to the amine and then being cyclized under the influence of acids and aromatized with an oxidizing agent, such as arsenopentoxide, iron(III) oxide or picric acid. The reaction is performed at temperatures from room temperature to 150° C. in inert solvents, such as toluene, xylene.

To produce an imidazole, for example, the corresponding amino-β-carboline derivative is condensed with a primary amine $R^5$—$CH_2$—$NH_2$ in the presence of an oxidizing agent, such as $MnO_2$, at room temperature or elevated temperature in inert solvents, such as dichloromethane, dichloroethane or ethylene glycol dimethyl ether.

The pyrrolocarboline can be produced from, e.g., the ethylene hydrazino-β-carboline derivative, by the latter being heated in an inert solvent, such as hydrocarbons, e.g., toluene, xylene, benzene, in the presence of organic or inorganic acids or polyphosphoric acid esters.

The production of the ethylene hydrazino starting compounds can be carried out with the aid of the Sandmeyer reaction, by, e.g., the diazonium salts formed intermediately from the amino compounds with nitrites being reacted with alkali salts of the acetoacetic acid esters in protic solvents, such as water or alcohols, at temperatures of 0° C. up to room temperature.

Thiazolo-carbolines can be produced, for example, by reaction of the compounds of formula V with thiocyanate or isothiocyanate compounds. The reaction is carried out suitably in an inert solvent in the presence of an organic or inorganic acid, whereby if an organic acid is used, the latter can be used as solvent. For cyclization, in general an oxidizing agent, such as, for example, bromine, is added. Starting from hydroxy-β-carbolines, oxazolocarbolines are obtained analogously to the Scraup synthesis that is described above by reacting a primary amine in the presence of an oxidizing agent such as $MnO_2$ at room temperature or elevated temperature in an inert solvent. If a vicinal primary diamino compound is used in the reaction instead of a primary amine, the corresponding pyrazine derivatives, whose isomer mixtures can be separated in the usual way such as chromatographically or by fractionated crystallization, are obtained.

The reaction of the nitrile oxides of formula VII with the acetylene derivatives can be carried out, for example, according to the methods that are described by K. G. B. Torsell (K. G. B. Torsell, Nitrile Oxides, Nitrones and Nitronates in Organic Synthesis, 1988 VCH Verlagsgesellschaft mbH). In this connection, generally first the nitrile oxide is produced, which then is reacted with an acetylene derivative without isolation.

The molar ratios of nitrile oxide and acetylene can vary within limits. In general, approximately equal molar amounts of the reactants are used, but it can often also be advantageous to use more of the acetylene derivative. The reaction is performed in an aprotic solvent at temperatures of −78° C. to 150° C., preferably −20° C. to 50° C.

As solvents, for example, aliphatic and cyclic ethers, such as diethyl ether, tetrahydrofuran, dioxane, halogenated hydrocarbons, such as dichloroethane, methylene chloride, chloroform, hydrocarbons, such as hexane, pentane and dimethylformamide, dimethyl sulfoxide, are suitable.

If the starting compounds are gaseous, such as, for example, acetylene, it is advantageous to use in the reaction the corresponding liquid compounds, which have a then easily cleavable group. As an easily cleavable group, for example, the trialkylsilyl group is suitable. The cleavage is carried out before the working-up of the reaction mixture according to the known methods, such as, for example, by adding bases at room temperature. Suitable bases are, for example, alkali hydroxides and alkali alcoholates, such as sodium or potassium hydroxide, methylate or ethylate, or fluorides, such as cesium fluoride or tetra-n-butylammonium fluoride.

B-carboline derivatives protected in 9-position optionally can be used in the reaction. The protective group is to be cleaved in the usual way in the working-up of the reaction mixture or subsequently by treatment with bases or acids depending on the type of protective group.

The production of the nitrile oxides is carried out, for example, by reacting β-carboline-3-carbaldehydes to the corresponding oximes, which can be converted to hydroxamic acid halides, for example, with N-halosuccinimide, tert-butoxychlorite or Na-halosuccinimide, tert-butoxychlorite, or Na-hypochlorite in aprotic solvents. With bases such as Na- or K-alcoholates, trialkylamines, Hunig base, DBU or diazabicyclooctane, hydrogen halide is cleaved from the hydroxamic acid halides, and nitrile oxides, which are discarded without isolation or cycloaddition, are obtained (R. Annunziata et al., J. Chem. Soc. 1987, 529).

The production of the β-carboline-3-carbaldehydes can be carried out, for example, according to the process that is described in EP-305 322 from the β-carboline-3-carboxylic acid alkyl esters.

The reaction with α-haloketones according to process f) is carried out according to the methods that are described in The Chemistry of Heterocyclic Compounds Vol. 34 Part 1, page 180 ff (1979). For example, the thioamide in solution or in suspension is reacted with the α-haloketone, especially the chloroketone or bromoketone, at temperatures up to the boiling temperature of the reaction mixture. As inert solvents, alcohols, cyclic and acyclic ethers, esters, hydrocarbons and halogenated hydrocarbons are suitable.

The production of the 3-tetrazolyl-β-carbolines can be carried out, for example, according to the process with $HN_3$ that is described in EP-A-54507 or according to the methods that are described in E. W. Thomas, Synthesis (1993), page 767, P. Ornstein et al. J. Med. Chem. 36 2046, (1993).

The hydrolysis of an ester group can be carried out in an acid or alkaline manner in the usual way, for example, with aqueous alkali or alkaline-earth solutions, optionally by adding organic solvents, such as alcohols, at temperatures from room temperature to 150° C. or according to the processes that are described in EP-A-161 574.

If a re-esterification is desired, the methods that are described in EP-A-237 467 can be used, by the re-esterification taking place with alkali alcoholates or the corresponding alcohol, optionally by adding titanium-tetraisopropylate as catalyst at elevated temperature. The introduction of the tert-butyl ester group is carried out by, e.g., reaction of carboxylic acid with tert-butoxy-bis-dimethyl-aminomethane.

The esterification of the carboxylic acid takes place in a way known in the art, for example, with the corresponding alcohol in acid or in the presence of an activated acid derivative. As activated acid derivatives, for example, acid chloride, acid imidazolide or acid anhydride are suitable.

If an alkylation of the amino group is desired, alkylation can be performed according to usual methods, for example, with alkyl halides. The acylation of the amino group is carried out according to the known methods. For example, it is reacted in an aqueous medium in the presence of a base with the corresponding acid anhydrides or acid halides.

The release of the functionally modified hydroxy group is carried out according to the methods that are known to one skilled in the art. For example, the cleavage of ether protective groups is performed in an aqueous solution of an organic acid, such as, for example, formic acid, acetic acid, propionic acid, trifluoroacetic acid, citric acids, i.a., or in an aqueous solution of an inorganic acid, such as, for example, hydrochloric acid, or by using Lewis acids, such as boron trifluoride etherate.

Silyl protective groups can be removed, for example, with fluorides, such as tetrabutylammonium fluoride or cesium fluoride.

The saponification of acyl groups is performed according to the methods that are known to one skilled in the art, such as, for example, with basic catalysts, such as, for example, with alkali or alkaline-earth carbonates or -hydroxides in an alcohol or the aqueous solution of an alcohol.

The compounds of formula I can be isolated from the reaction mixture and purified in a way known in the art. Acid addition salts can be converted into the free bases in the usual way, and the latter optionally in a known way into physiologically compatible acid addition salts, for example, by the solution being mixed with a concentrated solution of the desired acid.

If the compounds of formula I contain a chiral center, the optically active compounds can be obtained starting from optically active starting compounds or from the racemates in a way known in the art. The separation of enantiomers can be carried out by, for example, chromatography on optically active vehicles, by reaction with optically active acids and subsequently fractionated crystallization.

For the formation of physiologically compatible acid addition salts, a compound of formula I is dissolved, for example, in a little alcohol and mixed with a concentrated solution of the desired acid.

In so far as the production of the starting compounds is not described, the latter are known or can be produced analogously to known compounds or the processes that are described here.

For example, the production of 3-carboxylic acid esters of formula VI is described in EP-A-130 140, and the production of compounds of formula V is described in EP-A-54 507.

The affinity to the benzodiazepine receptors is determined by studying the ability of test substances to displace radio-labeled benzodiazepines from a benzodiazepine receptor. To study the anxiolytic effect, the compounds are tested in the 4-plate test according to the method of Boissier et al. Eur. J. Pharmacol. 4, 145–150 (1968).

The antiamnestic action can be tested (DMTP test) according to the method of B. J. Cole et al. Psychopharmacology (1993) 111:465–471, and attentiveness can be tested according to the method of J. L. Muir et al. Exp. Brain Res (1982) 89:611–622 (9-hole box).

Thus, for example, isopropyl-11-methoxymethyl-3-methyl-pyrazino[2,3-g]-β-carboline-10-carboxylate in "Behavioural Tests of Learning and Memory" (e.g., according to Cole et al., 1994, Psychopharmacol. 116, 135–142) in rats at doses of 10 mg/kg i.p. shows an improvement in cognitive performance.

The following examples are to explain the process according to the invention:

EXAMPLE 1

Isopropyl-11-ethyl-3-methyl-pyrazino[2,3-g]-β-carboline-10-carboline and isopropyl-11-ethyl-2-methyl-pyrazino[2,3-g]-β-carboline-10-carboxylate 20 g of isopropyl-4-ethyl-6-hydroxy-β-carboline-3-carboxylate is dissolved in 800 ml of ethylene glycol dimethyl ether (DME) and 7.2 ml of 1,2-diaminopropane while nitrogen is introduced at room temperature. While being stirred, 175 g of manganese(IV) oxide is introduced in portions into the solution within 30 minutes, so that the reaction temperature does not rise above 28° C. After the addition of manganese(IV) oxide is completed, another 2.9 ml of 1,2-diaminopropane is added. The reaction mixture is stirred under nitrogen atmosphere overnight. The reaction mixture is filtered on diatomaceous earth, and the filter residue is rewashed five times with 100 ml of DME each. The combined filtrates are evaporated almost to dryness, and the precipitated crystals are isolated. The crude crystallizate obtained is recrystallized three times from methanol.

9.5 g of isopropyl-11-ethyl-3-methyl-pyrazino[2,3-g]-β-carboline-10-carboxylate with a melting point of 236.5–237.5° C. is obtained.

The combined mother liquors are evaporated to dryness and then boiled out with isopropyl acetate. The undissolved residue is filtered off and recrystallized four times from methanol.

265 mg of isopropyl-11-ethyl-2-methyl-pyrazino[2,3-g]-β-carboline-10-carboxylate with a melting point of 215–216° C. is obtained.

Analogously, there are produced:

Isopropyl-11-methoxymethyl-3-ethyl-pyrazino[2,3-g]-β-carboline-10-carboxylate melting point 202–203° C.

isopropyl-11-methyl-3-ethyl-pyrazino[2,3-g]-β-carboline-10-carboxylate melting point 204–206° C.

isopropyl-3,11-diethyl-pyrazino[2,3-g]-β-carboline-10-carboxylate melting point 188–190° C.

isopropyl-11-methoxymethyl-pyrazino[2,3-g]-β-carboline-10-carboxylate melting point 238° C. (decomposition)

isopropyl-11-methoxymethyl-2,3,4,5-tetrahydroquinoxalino-[2,3-g]-β-carboline-12-carboxylate melting point 224–225° C. (decomposition)

isopropyl-11-methoxymethyl-3-phenyl-pyrazino[2,3-g]-carboline-10-carboxylate melting point 262–263° C.

isopropyl-11-ethyl-3-phenyl-pyrazino[2,3-g]-β-carboline-10-carboxylate melting point 235–236° C.

isopropyl-11-methoxymethyl-pyrazino[2,3-g]-β-carboline-10-carboxylate melting point 195–197° C.

isopropyl-2,11-dimethyl-pyrazino[2,3-g]-β-carboline-10-carboxylate melting point 155–160° C.

isopropyl-11-methoxymethyl-2,3-dimethyl-pyrazino[2,3-g)-β-carboline-10-carboxylate melting point 244–245° C.

isopropyl-11-ethyl-2,3-dimethyl-pyrazino[2,3-g]-β-carboline-10-carboxylate melting point 233–236° C.

isopropyl-11-methyl-2,3-dimethyl-pyrazino[2,3-g]-β-carboline-10-carboxylate melting point 305° C. (decomposition)

isopropyl-11-methoxymethyl-3-propyl-pyrazino[2,3-g]-β-carboline-10-carboxylate melting point 172–173° C.

isopropyl-11-ethyl-3-propyl-pyrazino[2,3-g]-β-carboline-10-carboxylate melting point 184–186° C.

isopropyl-11-ethyl-3-methoxymethyl-pyrazino[2,3-g]-β-carboline-10-carboxylate melting point 198–199° C.

isopropyl-3,11-bis(methoxymethyl)-pyrazino[2,3-g]-β-carboline-10-carboxylate melting point 193–194° C.

EXAMPLE 2

7H-Benzo[e]pyrido[3,4]-indole-10-carboxylic acid ethyl ester

Analogously to the process in Example 1 of EP-110 813, the title compound with a melting point of 278–280° C. is obtained from 3H-benz[e]indole and 3-dimethylamino-2-(dimethylaminomethyleneamino-acrylic acid ethyl ester (azadiene 1).

EXAMPLE 3

7H-Benzo[e]pyrido[3,4-b]-indole-11-methoxymethyl-10-carboxylic acid-isopropyl ester a) Analogously to the process in Example 19 of EP-A-54 507, the 7H-benzo[e]pyrido[3,4-b]-indole-11-methoxymethyl-10-carboxylic acid ethyl ester with a melting point of 195–197° C. is obtained from 3H-benz[e]indole.

b) By re-esterification with titanium(IV) isopropylate, the title compound with a melting point of 163–164° C. is obtained from the ethyl ester.

EXAMPLE 4

7H-Benzo[e]pyrido[3,4-b]-indole-1]-methyl-10-carboxylic acid isopropyl ester a) Analogously to the process in Example 60 of EP-A-54 507, the 7H-benzo[e]pyrido[3,4-b]-indole-11-methyl-10-carboxylic acid ethyl ester with a melting point of 244–246° C. is obtained from 3H-benz[e]indole.

b) By re-esterification with titanium(IV) isopropylate, the title compound with a melting point of 171–173° C. is obtained from the ethyl ester.

EXAMPLE 5

7H-Benzo[e]pyrido[3,4-b]-indole-11-ethyl-10-carboxylic acid isopropyl ester a) Analogously to the process in Example 60 of EP-A-54 507, the 7H-benzo[e]pyrido[3,4-b]indole-11-ethyl-10-carboxylic acid ethyl ester with a melting point of 201–205° C. is obtained from 3H-benz[e]indole.

b) By re-esterification with titanium(IV) isopropylate, the title compound with a melting point of 193–196° C. is obtained from the ethyl ester.

EXAMPLE 6

10-Methyl-2-propyl-oxazolo[4,5-g]-β-carboline-9-carboxylic acid isopropyl ester

A solution of 570 mg of 6-hydroxy-4-methyl-β-carboline-3-carboxylic acid isopropyl ester in 15 ml of ethylene glycol dimethyl ether is mixed with 1 ml of n-butylamine and 5.2 g of manganese dioxide, and it is stirred overnight at room temperature. The reaction mixture is filtered on Celite. After the organic phase is concentrated by evaporation, the remaining residue is chromatographed on silica gel with ethyl acetate. The desired fractions are concentrated by evaporation and absorptively precipitated with ether.

325 mg of 10-methyl-2-propyl-oxazolo[4,5-g]-β-carboline-9-carboxylic acid isopropyl ester with a melting point of 223–224° C. is obtained.

Analogously, there are produced:

10-Ethyl-2-isopropyl-oxazolo[4,5-g]-β-carboline-9-carboxylic acid isopropyl ester melting point 205–207° C.

10-ethyl-2-propyl-oxazolo[4,5-g]-β-carboline-9-carboxylic acid isopropyl ester melting point 163–165° C.

10-methyl-2-isopropyl-oxazolo[4,5-g]-β-carboline-9-carboxylic acid isopropyl ester melting point 248–249° C.

10-methoxymethyl-2-ethyl-oxazolo[4,5-g]-β-carboline-9-carboxylic acid isopropyl ester melting point 188–189° C.

10-methoxymethyl-2-methyl-oxazolo[4,5-g]-β-carboline-9-carboxylic acid isopropyl ester melting point 191–193° C.

10-methoxymethyl-2-pentyl-oxazolo[4,5-g]-β-carboline-9-carboxylic acid isopropyl ester melting point 188–190° C.

10-methoxymethyl-2-isopropyl-oxazolo[4,5-g]-β-carboline-9-carboxylic acid isopropyl ester melting point 174–176° C.

10-methoxymethyl-2-phenyl-oxazolo[4,5-g]-β-carboline-9-carboxylic acid isopropyl ester melting point 274–276° C.

10-methoxymethyl-2-propyl-oxazolo[4,5-g]-β-carboline-9-carboxylic acid isopropyl ester melting point 188–189° C.

10-methoxymethyl-2-(2,2-dimethyl-1,3-dioxolan-4-yl)-oxazolo[4,5-g]-β-carboline-9-carboxylic acid isopropyl ester melting point 202–203° C.

2-(2,2-dimethyl-1,3-dioxolan-4-yl)-10-methyl-oxazolo[4,5-g]-β-carboline-9-carboxylic acid isopropyl ester melting point 278–280° C.

2-(2,2-dimethyl-1,3-dioxolan-4-yl)-10-ethyl-oxazolo-[4,5-g]-β-carboline-9-carboxylic acid isopropyl ester melting point 228–230° C.

EXAMPLE 7

2-(1,2-Dihydroxyethyl)-10-methoxymethyl-oxazolo-[4,5-g]-β-carboline-9-carboxylic acid isopropyl ester A solution of 200 mg of 2-(2,2-dimethyl-1,3-dioxolan-4-yl)-10-methoxymethyl-oxazolo-[4,5-g]-β-carboline-9- carboxylic acid isopropyl ester in 20 ml of methylene chloride is mixed drop by drop at room temperature with 1 ml of trifluoroacetic acid, and it is stirred at room temperature under protective gas for another 4 hours. The reaction solution is neutralized with the equimolar amount of sodium bicarbonate solution. The precipitated solid product is suctioned off and washed with methylene chloride. After the drying in a vacuum at 50° C., 112 mg of 2-(1,2-dihydroxyethyl)-10-methoxymethyl-oxazolo-[4,5-g]-β-carboline- 9-carboxylic acid isopropyl ester with a melting point of 168° C. (decomposition) is obtained.

Analogously, there are produced:

2-(1,2-Dihydroxyethyl)-10-methyl-oxazolo-[4,5-g]-β-carboline-9-carboxylic acid isopropyl ester melting point 195–196° C. (decomposition)

2-(1,2-dihydroxylethyl)-10-ethyl-oxazolo-[4,5-g]-β-carboline-9-carboxylic acid isopropyl ester melting point 184–186° C. (decomposition)

EXAMPLE 8

10-Methoxymethyl-2-isopropyl-oxazolo-[4,5-g]-9-(5-methoxymethyl-3-isoxazolyl)-β-carboline 10-Methoxymethyl-2-isopropyl-oxazolo[4,5-g]6-tosyl-β-carboline-3-carbaldehydoxime hydrochloride in 6 ml of absolute tetrahydrofuran is added in drops to 1.4 ml of sodium hypochloride solution at room temperature under protective gas. It is stirred until the oxime has disappeared (TLC control) for 1 hour at room temperature, then 210 mg of methyl propargyl ether is added in drops and stirred overnight. After the solvent is distilled off, it is dispersed in ethyl acetate/water, and the organic phase is dried, filtered and concentrated by evaporation. The residue is dissolved in 8 ml of methanol, mixed with 60 mg of sodium methylate and refluxed for 1 hour. After the organic phase is concentrated by evaporation, the residue is chromatographed on silica gel and toluene: ethyl acetate=1:1. The desired fractions are concentrated by evaporation and crystallized from ethyl acetate. 81 mg of 10-methoxymethyl-2-isopropyl-oxazolo[4,5-g]-9-(5-methoxymethyl-3-isoxazolyl)-β-carboline with a melting point of 121–122° C. is obtained.

The carbaldehydoxime hydrochloride required as starting material is produced according to the process that is described in patent EP 0305 322.

Analogously, there is produced:

10-Methoxymethyl-2-isopropyl-oxazolo[4,5-g]-9-(5-methyl-3-isoxazolyl)-β-carboline melting point 252–255° C.

EXAMPLE 9

2-Amino-10-ethyl-thiazolo[4,5-g]-β-carboline-9-carboxylic acid isopropyl ester 297 mg of 6-amino-4-ethyl-β-carboline-3-carboxylic acid isopropyl ester is dissolved in 5 ml of acetic acid, mixed with 152 mg of ammonium thiocyanate and stirred for 1 hour at room temperature. Then, the reaction solution is cooled to 10° C. and mixed drop by drop with 0.05 ml of acetic bromine solution (0.5 ml of $BR_2$ in 9.5 ml of acetic acid). It is stirred for 1 more hour at 10° C. and then heated to room temperature. The reaction mixture is taken up in ethyl acetate/water and neutralized with 10% $K_2CO_3$ solution. The organic phase is separated, dried and evaporated to dryness. The residue is triturated with ether. 214 mg of the title compound with a melting point of 160° C. (decomposition) is obtained.

EXAMPLE 10

2-Amino-10-methoxymethyl-thiazolo[4,5-g]-β-carboline-9-carboxylic acid isopropyl ester According to the process that is described in Example 9, the title compound with a melting point of 188–192° C. (decomposition) is obtained from 6-amino-4-methoxymethyl-β-carboline-3-carboxylic acid isopropyl ester.

EXAMPLE 11

2-Acetamido-10-ethyl-thiazolo[4,5-g]-β-carboline-9-carboxylic acid isopropyl ester 100 mg of 2-amino-10-ethyl-thiazolo[4,5-g]-β-carboline-9-carboxylic acid isopropyl ester is suspended in 10 ml of acetic anhydride and heated for 15 minutes to 80° C. After cooling, the settled precipitate is filtered off and recrystallized from ethyl acetate. 51 mg of 2-acetamido-10-ethyl-thiazolo[4,5-g]-β-carboline-9-carboxylic acid isopropyl ester with a melting point of 208–210° C. is obtained.

EXAMPLE 12

2-Ethylamino-10-ethyl-thiazolo[4,5-g]-β-carboline-9-carboxylic acid isopropyl ester a) 297 mg of 6-amino-4-ethyl-β-carboline-3-carboxylic acid isopropyl ester and 88 mg of methyl isothiocyanate are refluxed for 2 hours in 20 ml of isopropanol. The solvent is distilled off in a vacuum, and the residue is recrystallized from ethyl acetate/ether. 257 mg of 4-ethyl-6-(3-ethyl-thioureido)-β-carboline- 3-carboxylic acid-isopropyl ester with a melting point of 234–236° C. is obtained.

b) 0.035 ml of bromine is added in drops at room temperature to a suspension of 180 mg of 4-ethyl-6-(3-ethyl-thioureido)-β-carboline-3-carboxylic acid isopropyl ester in 20 ml of chloroform and then refluxed for 3 hours. The reaction solution is concentrated by evaporation and taken up in ethyl acetate and 20% aqueous $K_2CO_3$ solution. The organic phase is separated, dried and concentrated by evaporation. The residue is recrystallized from ethyl acetate. 141 mg of the title compound with a melting point of 275–276° C. is obtained.

EXAMPLE 13

Analogously to the process that is described in Example 11, there are produced:

2-Methylamino-10-ethyl-thiazolo[4,5-g]-β-carboline-9-carboxylic acid isopropyl ester melting point 200° C. (decomposition)

2-methylamino-10-methyl-thiazolo[4,5-g]-β-carboline-9-carboxylic acid isopropyl ester 2-methylamino-10-methoxymethyl-thiazolo[4,5-g]-β-carboline-9-carboxylic acid isopropyl ester

EXAMPLE 14

Pyrrolo[4,5-g]-β-carboline-2,5-dicarboxylic acid diethyl ester a) 710 mg of 6-amino-β-carboline-3-carboxylic acid ethyl ester is mixed in 18 ml of water at 4° C. with 1.2 ml of concentrated hydrochloric acid. A solution of 210 mg of sodium nitrite in 20 ml of water is added in drops to the precipitated salt, and it is stirred for another 15 minutes at 4° C. This solution is added in drops at 4° C. to 410 mg of ethyl-2-methylacetoacetate and 1 ml of 50% KOH in 3 ml of ethanol and 6 ml of water, and it is stirred for another 3 hours. The reaction mixture is mixed with 50 ml of water and extracted with ethyl acetate. The organic phases are washed with water, dried, and concentrated by evaporation. 250 mg of 6-(1-ethoxy-carbonyl-ethylidenehydrazino)-β-carboline-3-carboxylic acid ethyl ester is obtained, which is processed without further purification.

b) 750 mg of 6-(1-ethoxycarbonylethylidenehydrazino)-β-carboline-3-carboxylic acid ethyl ester is refluxed with 1.83 g of polyphosphoric acid ethyl ester in 35 ml of absolute xylene under protective gas for 2 hours. After cooling, the xylene is decanted, and the residue is taken up in ethyl acetate, filtered on Celite and concentrated by evaporation. The residue obtained is chromatographed on silica gel with ethanol. The desired fractions are concentrated by evaporation and recrystallized from ethanol. 45 mg of the title compound with a melting point of 198–201° C. is obtained.

EXAMPLE 15

2-Isopropyl-10-methoxymethyl-1H-imidazo[4,5-g]-β-carboline-9-carboxylic acid isopropyl ester 627 mg of 6-amino-4-methoxymethyl-β-carboline-3-carboxylic acid isopropyl ester is stirred in 10 ml of ethylene glycol dimethyl ether with 1.6 g of manganese dioxide and 0.98 ml of isobutylamine for 16 hours at room temperature. The reaction mixture is filtered on Celite, the filtrate is concentrated by evaporation and chromatographed on silica gel with methylene chloride and ethanol=10+1. 499 mg of 2-isopropyl-10-methoxymethyl-1H-imidazo[4,5-g]-β-carboline-9-carboxylic acid isopropyl ester (oily) is obtained from the desired fractions.

Analogously, there are produced:

2-Isopropyl-10-methyl-1H-imidazo[4,5-g]-β-carboline-9-carboxylic acid isopropyl ester 2-isopropyl-10-ethyl-1H-imidazo[4,5-g]-β-carboline-9-carboxylic acid isopropyl ester 2-phenyl-10-methoxymethyl-1H-imidazo[4,5-g]-β-carboline-9-carboxylic acid isopropyl ester 2-butyl-10-methoxymethyl-1H-imidazo[4,5-g]-β-carboline-9-carboxylic acid isopropyl ester 2-(2,2-dimethyl-1,3-dioxolan-4-yl)-10-ethyl-1H-imidazo[4,5-g]-β-carboline-9-carboxylic acid isopropyl ester 2-(2,2-dimethyl-1,3-dioxolan-4-yl)-10-methoxymethyl-1H-imidazo[4,5-g]-β-carboline-9-carboxylic acid isopropyl ester 2-ethyl-10-methoxymethyl-1H-imidazo[4,5-g]-β-carboline-9-carboxylic acid isopropyl ester 10-methoxymethyl-2-trifluoromethyl-1H-imidazo[4,5-g]-β-carboline-9-carboxylic acid isopropyl ester 10-methoxymethyl-2-(2-thienyl)-1H-imidazo[4,5-g]-β-carboline-9-carboxylic acid isopropyl ester 2-(2-furyl)-10-methoxymethyl-1H-imidazo[4,5-g]-β-carboline-9-carboxylic acid isopropyl ester 2-(4-chlorophenyl)-10-methoxymethyl-1H-imidazo[4,5-g]-β-carboline-9-carboxylic acid isopropyl ester melting point 270° C. (decomposition)

2-(2-chlorophenyl)-10-methoxymethyl-1H-imidazo[4,5-g]-β-carboline-9-carboxylic acid isopropyl ester melting point 205–207° C.

2-(4-methylphenyl)-10-methoxymethyl-1H-imidazo[4,5-g]-β-carboline-9-carboxylic acid isopropyl ester melting point 168° C. (decomposition)

2-(4-methoxyphenyl)-10-methoxymethyl-1H-imidazo[4,5-g]-β-carboline-9-carboxylic acid isopropyl ester melting point 258–260° C.

2-(2-methoxyphenyl)-10-methoxymethyl-1H-imidazo[4,5-g]-β-carboline-9-carboxylic acid isopropyl ester melting point 225–228° C.

EXAMPLE 16

Analogously to the process that is described in Example 7, there are produced:

2-(1,2-Dihydroxyethyl)-10-methoxymethyl-1H-imidazo[4,5-g]-β-carboline-9-carboxylic acid isopropyl ester melting point 198° C.

2-(1,2-dihydroxyethyl)-10-ethyl-1H-imidazo[4,5-g]-β-carboline-9-carboxylic acid isopropyl ester melting point 168° C.

EXAMPLE 17

10-Ethyl-2-methyl-thiazolo[5,4-g]-β-carboline-9-carboxylic acid isopropyl ester a) 2500 mg of 6-amino-4-ethyl-β-carboline-3-carboxylic acid isopropyl ester is dissolved in 40 ml of pyridine, mixed with 0.79 ml of acetic anhydride and heated for 2 hours to 50° C. After 20 ml of water is added, it is concentrated by evaporation in a vacuum. The residue is dissolved in ethyl acetate and washed with water. The organic phase is separated, dried and evaporated to dryness. The residue, 3110 mg of 6-acetylamino-4-ethyl-β-carboline-3-carboxylic acid isopropyl ester, is processed without further purification.

b) 2741 mg of 6-acetylamino-4-ethyl-β-carboline-3-carboxylic acid isopropyl ester is heated to 70° C. in 110 ml of dioxane with 3915 mg of Lawesson's reagent while being stirred. After cooling, it is mixed with 100 ml of ethyl acetate and washed with saturated sodium chloride solution. The organic phases are dried and concentrated by evaporation in a vacuum. The residue is chromatographed on silica gel with toluene+methanol=8+2. 1541 mg of 4-ethyl-6-thioacetylamino-β-carboline-3-carboxylic acid isopropyl ester with a melting point of 158–160° C. is obtained from the desired fractions.

c) 450 mg of $K_3Fe(CN)_6$ is dissolved in 1.8 ml of water, mixed with 1.4 ml of 1N NaOH and cooled to 4° C. 200 mg of 4-ethyl-6-thioacetylamino-β-carboline-3-carboxylic acid isopropyl ester in 4 ml of pyridine is added in drops to this solution and stirred for another 2 hours at this temperature. The reaction mixture is taken up in ethyl acetate, washed with water, dried and concentrated by evaporation. The residue is chromatographed on silica gel with toluene+ethanol=95+5. The desired fractions are concentrated by evaporation and stirred up with ether. 30 mg of the title compound with a melting point of 239–240° C. is obtained.

What is claimed is:

1. A compound of the formulae I, or an isomer, tautomer or salt thereof

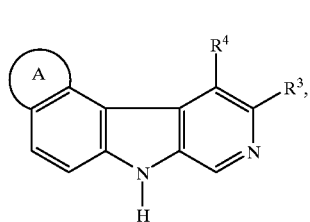

(I)

-continued

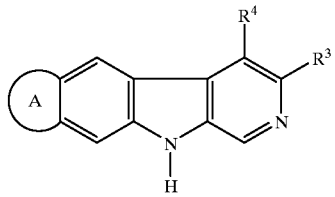

in which

R³ means hydrogen, $C_{1-6}$ alkyl, —CO—R¹, —C≡N, phenyl which optionally is substituted one to three times with $C_{1-4}$ alkyl, $C_{1-4}$ alkoxy, halogen or —CF₃,

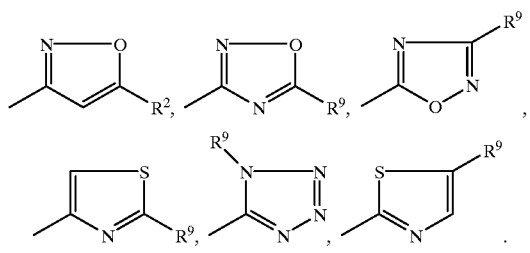

R⁴ means hydrogen, $C_{1-6}$ alkyl, or $C_{1-4}$ alkoxy-$C_{1-2}$ alkyl, provided that R³ and R⁴ are not simultaneously hydrogen, and A represents a 5- to 6-membered unsaturated ring, in which 1–2 C atoms are optionally replaced by N, O and/or S and which is optionally substituted by R⁵ and R⁶, where R⁵ and R⁶ are the same or different and mean hydrogen, $C_{1-6}$ alkyl, $C_{1-6}$ alkoxy, hydroxy which is optionally functionally modified, NR⁷R⁸, COR, $C_{1-6}$ alkyl substituted with optionally functionally modified hydroxy, $C_{1-4}$ alkoxy or halogens, a $C_{6-12}$ aryl or a 5- to 6-membered hetaryl radical which contains one to three N, O and/or S atoms, the aryl and hetaryl radical optionally being substituted with $C_{1-4}$ alkyl, $C_{1-4}$ alkoxy, hetaryl or CF₃, or R⁵ and R⁶ together mean a —(CH₂)ₙ— group and R¹ and R mean hydroxy, $C_{1-6}$ alkoxy or NR¹⁰R¹¹, R² means hydrogen, $C_{1-4}$ alkyl or $C_{1-4}$ alkoxy-$C_{1-2}$ alkyl, R⁹ means hydrogen or $C_{1-6}$ alkyl, n means 3 or 4, R⁷ or R⁸ each mean hydrogen, $C_{1-6}$ alkyl, acyl or phenyl which is optionally substituted singly or repeatedly with $C_{1-4}$ alkyl, $C_{1-4}$ alkoxy, halogen or CF₃, R¹⁰ and R¹¹ each mean hydrogen, $C_{1-6}$ alkyl, $C_{3-7}$ cycloalkyl or a $C_{6-12}$ aryl radical or a 5- to 6-membered hetaryl radical, which contains one to three N, O and/or S atoms, and the aryl and hetaryl radicals are optionally substituted singly or repeatedly with $C_{1-4}$ alkyl, $C_{1-4}$ alkoxy, halogen or CF₃.

2. A compound according to claim 1, in which A means ——N=CR⁵—CR⁶=N——.

3. A compound of claim 1, which is:

isopropyl-11-ethyl-3-methyl-pyrazino-[2,3g]-β-carboline-10-carboxylate, isopropyl-11-ethyl-2-methyl-pyrazino-[2,3-g]β-carboline-10-carboxylate, isopropyl-11-methoxymethyl-2,3,4,5-tetrahydroquinoxalino-[2,3g]β-carboline-12-carboxylate, isopropyl-3,11-bis(methoxymethyl)-pyrazino-[2,3-g]β-carboline-10-carboxylate, 7H-benzo[e]pyrido[3,4-b]-indole-11-methoxymethyl-10-carboxylic acid-isopropyl ester, 10-methyl-2-propyl-oxazolo[4,5-g]-β-carboline-9-carboxylic acid isopropyl ester, 2-(1,2-dihydroxyethyl)-10-methoxymethyl-oxazolo-[4,5-g]-β-carboline-9-carboxylic acid isopropyl ester, 10-methoxymethyl-2-isopropyl-oxazolo-[4,5-g]-9-(5-methoxymethyl-3-isoxazolyl)-β-carboline, 2-amino-10-ethyl-thiazolo[4,5-g]-β-carboline-9-carboxylic acid isopropyl ester, 2-amino-10-methoxymethyl-thiazolo[4,5-g]-β-carboline-9-carboxylic acid isopropyl ester, pyrrolo[4,5-g]-β-carboline-2,5-dicarboxylic acid diethyl ester, 2-isopropyl-10-methoxymethyl-1H-imidazo[4,5-g]-β-carboline-9-carboxylic acid isopropyl ester or 10-ethyl-2-methyl-thiazolo[5,4-g]-β-carboline-9-carboxylic acid isopropyl ester.

4. A process for the production of a compound according to claim 1, which comprises:

a) reacting a compound of formula II

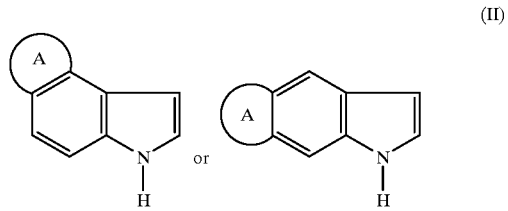

with a 2-azadiene of formula III

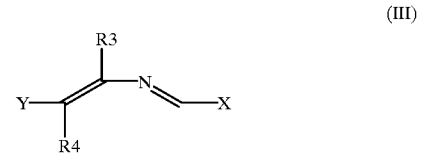

in which R³, R⁴ and A have the above meaning, and X and Y represent leaving groups, in the presence of acids or b) aromatizing a compound of formula IV

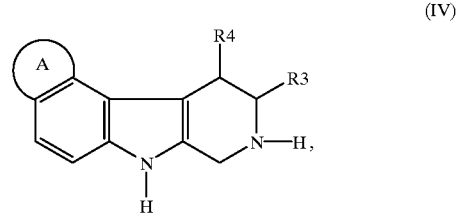

-continued

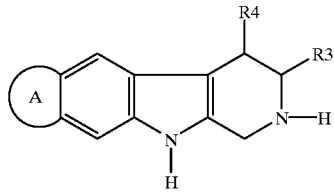

in which $R^3$, $R^4$ and A have the above meaning, or c) reacting a compound of formula V (V)

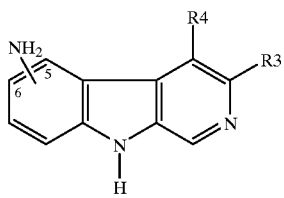

in which $R^3$ and $R^4$ have the above meaning, with an α,β-unsaturated aldehyde to a fused pyridine or with a primary amine $H_2N-CH_2-R^5$ to a fused imidazole or reacting the diazonium salts obtained with nitrites with acetoacetic acid derivatives to an ethylidenehydrazine derivative and cyclizing the latter to the pyrrole or reacting a thiocyanate or isothiocyanate derivative to a fused thiazole or d) reacting a compound of formula VI (VI)

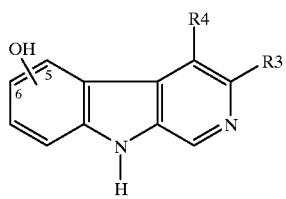

in which $R^3$ and $R^4$ have the above meaning, with a primary amine $H_2N-CH_2-R^5$ to a fused oxazole or with a vicinal primary diamine

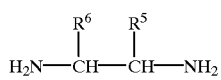

to a fused pyrazine or e) cyclizing a nitrile oxide of formula VII (VII)

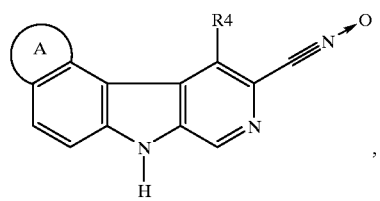

-continued

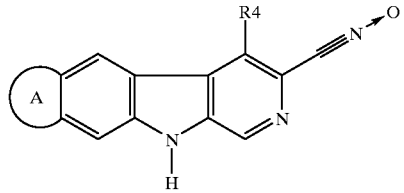

with $=\!\!-R^2$ to an isoxazole derivative, f) reacting an α-haloketone of formula VIII (VIII)

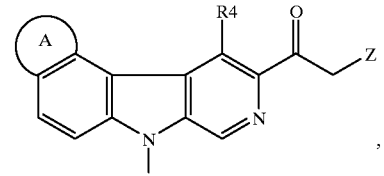

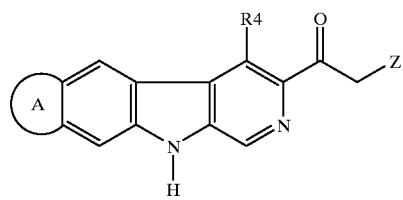

in which $R^4$ and A have the above meaning and Z is halogen, with a thioamide $H_2N-CS-R^9$ to a compound with $R^3$ meaning thiazolyl or g) cyclizing a nitrile of formula IX (IX)

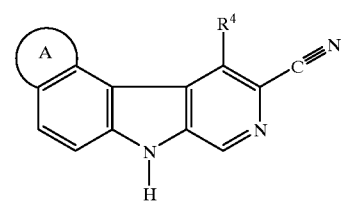

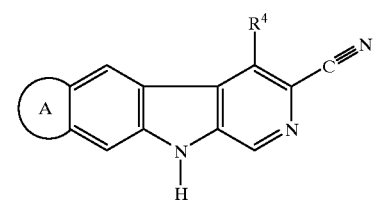

in which $R^4$ and A have the above meaning, with an azide to a compound with $R^3$ meaning tetrazolyl, and optionally then saponifying or reesterifying an ester group, esterifying a carboxyl group, alkylating or acylating an amino group, releasing a functionally modified hydroxy group, separating the isomers or forming a physiologically compatible salt.

5. A pharmaceutical composition which comprises a compound according to claim 1 or an isomer, tautomer or salt thereof, and at least one pharmaceutically acceptable vehicle and/or adjuvant.

6. A method for treating a condition or disease which comprises administering to a patient a composition according to claim 5 sufficient to produce anxiolytic, anti-amnestic and/or nootropic activity.

7. The method of claim 6, wherein the method is for improving learning or attentiveness.

8. The method of claim 6, wherein the method is for treatment of geriatric symptoms.

9. The method of claim 6, wherein the method is for mitigation of cognitive deficit and increase of vigilance.

10. The method of claim 6, wherein the compound according to claim 1 or an isomer, tautomer or salt thereof is administered in a daily dose of 0.1 to 300 mg.

11. A compound according to claim 1, which is the compound isopropyl-11-methoxymethyl-3-methyl-pyrazino[2,3-g]-β-carboline-10-carboxylate, isopropyl-11-ethyl-3-methyl-pyrazino[2,3-g]-β-carboline-10-carboxylate, or isopropyl-11-ethyl-2-methyl-pyrazino[2, 3-g]-β-carboline-10-carboxylate.

12. A compound of the formulae I, or an isomer, tautomer or salt thereof, according to claim 1, wherein A is a 5- or 6-membered unsaturated heterocycle ring having 1 or 2 N, O and/or S atoms in the ring and which is optionally substituted by $R^5$ and $R^6$.

13. A compound of the formulae I, or an isomer, tautomer or salt thereof, according to claim 1, wherein A is a 6-membered unsaturated heterocycle ring having 1 or 2 N atoms in the ring and which is optionally substituted by $R^5$ and $R^6$.

14. A compound of the formulae I, or an isomer, tautomer or salt thereof, according to claim 1, wherein $R^5$ and $R^6$ are the same or different and are hydrogen, $C_{1-6}$ alkyl or phenyl or $R^5$ and $R^6$ together are —$(CH_2)_{3-4}$—.

15. A compound of the formulae I, or an isomer, tautomer or salt thereof, according to claim 1, wherein $R^3$ is —$COR^1$.

16. A compound of the formulae I, or an isomer, tautomer or salt thereof, according to claim 1, wherein each aryl group, when present, is independently a phenyl, biphenyl or α- or β-naphthyl group.

17. A compound of the formulae I, or an isomer, tautomer or salt thereof, according to claim 1, wherein each hetaryl group, when present, is independently a triazine, pyridine, pyrimidine, pyrazine, pyridazine, furan, thiophene, pyrrole, imidazole, thiazole, 1,2,4-oxadiazolyl or 1,3,4-oxadiazolyl.

18. A compound of the formulae I, or an isomer, tautomer or salt thereof, according to claim 1, wherein each hetaryl group, when present, is independently a benzoyl of 1–6 carbon atom alkanoyl group.

19. A compound of the formulae I, or an isomer, tautomer or salt thereof, according to claim 1, wherein each functionally modified hydroxy group, when present, is independently an etherified or esterified hydroxy group.

* * * * *